(12) United States Patent
Maierhofer et al.

(10) Patent No.: US 8,465,641 B2
(45) Date of Patent: Jun. 18, 2013

(54) DIALYSIS LIQUID CIRCUIT, DIALYSIS APPARATUS COMPRISING A DIALYSIS LIQUID CIRCUIT, METHOD FOR DETECTING AIR IN A DIALYSIS LIQUID FLOWING THROUGH A DIALYSIS LIQUID CIRCUIT, AND USE OF A GAS SENSOR IN A DIALYSIS LIQUID CIRCUIT

(75) Inventors: Andreas Maierhofer, Schweinfurt (DE); Alfred Gagel, Litzendorf (DE); Malte Gross, Niederwerrn (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 518 days.

(21) Appl. No.: 12/452,956

(22) PCT Filed: Jul. 30, 2008

(86) PCT No.: PCT/EP2008/006285
§ 371 (c)(1),
(2), (4) Date: Jan. 29, 2010

(87) PCT Pub. No.: WO2009/015882
PCT Pub. Date: Feb. 5, 2009

(65) Prior Publication Data
US 2010/0133189 A1    Jun. 3, 2010

(30) Foreign Application Priority Data

Jul. 31, 2007   (DE) .......................... 10 2007 035 815
Jan. 22, 2008   (DE) .......................... 10 2008 005 516

(51) Int. Cl.
*B01D 61/30*   (2006.01)

(52) U.S. Cl.
USPC .................... 210/90; 210/85; 210/87; 210/97; 210/103; 210/109; 210/117; 210/130; 210/134; 210/136; 210/137; 210/143; 210/252; 210/258; 210/321.69

(58) Field of Classification Search
USPC .................... 210/85, 86, 87, 90, 97, 103, 109, 210/117, 130, 134, 136, 137, 143, 252, 257.2, 210/258, 321.6, 321.69
See application file for complete search history.

(56) References Cited

U.S. PATENT DOCUMENTS

| 4,085,046 A | | 4/1978 | Saporito, Jr. |
| 5,580,460 A | * | 12/1996 | Polaschegg ................... 210/646 |
| 5,783,072 A | | 7/1998 | Kenley et al. |

FOREIGN PATENT DOCUMENTS

| DE | 1 964 735 A1 | 7/1971 |
| DE | 196 51 355 A1 | 6/1998 |
| EP | 0 330 892 | 9/1989 |
| EP | 0 643 301 B1 | 3/1995 |
| GB | 1 326 236 A | 8/1973 |

(Continued)

*Primary Examiner* — John Kim
(74) *Attorney, Agent, or Firm* — Jacobson Holman PLLC

(57) ABSTRACT

A dialysis liquid circuit with conduits for conducting dialysis liquid and elements for detecting air in the dialysis liquid. The elements includes at least one gas sensor traversed continuously by the dialysis liquid, which is configured such that it measures at least one property of the dialysis liquid which depends on the presence of air bubbles in the dialysis liquid, and which is arranged downstream of a region to be monitored of the dialysis liquid circuit. During operation of the dialysis liquid circuit a negative pressure exists with respect to atmospheric pressure, and the elements includes an evaluation unit which is connected with the gas sensor and which is configured such that the property measured by means of the gas sensor is evaluated with regard to the presence of air bubbles in the dialysis liquid.

14 Claims, 2 Drawing Sheets

FOREIGN PATENT DOCUMENTS

| | | |
|---|---|---|
| JP | 1-270873 | 10/1989 |
| JP | 10-043290 | 2/1998 |
| WO | WO 96/04401 | 2/1996 |
| WO | WO 98/11430 | 3/1998 |

* cited by examiner

DIALYSIS LIQUID CIRCUIT, DIALYSIS APPARATUS COMPRISING A DIALYSIS LIQUID CIRCUIT, METHOD FOR DETECTING AIR IN A DIALYSIS LIQUID FLOWING THROUGH A DIALYSIS LIQUID CIRCUIT, AND USE OF A GAS SENSOR IN A DIALYSIS LIQUID CIRCUIT This is a national stage of PCT/EP08/006285 filed Jul. 30, 2008 and published in German, which has a priority of German no. 10 2007 035 815.8 filed Jul. 31, 2007 and German no. 10 2008 005 516.6 filed Jan. 22, 2008, hereby incorporated by reference.

BACKGROUND OF THE INVENTION

1. Field of Invention

The present invention relates to a dialysis liquid circuit with conduits for conducting dialysis liquid and with means for detecting air in the dialysis liquid.

2. Description of the Prior Art

The presence of air in a dialysis liquid conducted in a dialysis liquid circuit is undesirable in several respects. On the one hand, air bubbles can impede the measurement of the concentration of ingredients of the dialysis liquid, as is known from WO 96/04401. According to this document, it therefore is proposed to degas the dialysis liquid before measuring the concentration. On the other hand, air bubbles are disadvantageous for correctly balancing the dialysis liquids entering the dialyser and emerging from the same, since the commonly used balancing means employ a degassed dialysis liquid.

By level measurement in the air separation chamber, it is furthermore known to detect large amounts of air in the system. However, this does not provide a fast and reliable possibility for monitoring the dialysis liquid circuit for leakages.

For detecting leakages, leakage sensors are known which can, however, only be employed when there is a leakage of liquid. From the prior art it is furthermore known to detect leakages in the negative pressure region of the dialysis liquid circuit. For this purpose, the liquid circuit is stopped upon build-up of a negative pressure, the point to be examined is sealed and the course of pressure in time is measured. When the negative pressure is reduced, this is an indication for the penetration of air into the dialysis liquid circuit and hence for a leakage. According to this known method, pressure sensors and valves are necessary for sealing and limiting the region to be examined. A further disadvantage results from the fact that the liquid circulation must be stopped for the examination for leakages.

SUMMARY OF THE INVENTION

It is the object underlying the present invention to develop a dialysis liquid circuit as mentioned above such that with a comparatively small expenditure of apparatus leakages in the negative pressure region of the dialysis liquid circuit can be detected reliably and comfortably.

This object is solved by a dialysis liquid circuit with the features described herein.

Accordingly, it is provided that the means for detecting air in the dialysis liquid comprise at least one gas sensor traversed continuously by the dialysis liquid, which is configured such that it measures at least one property of the dialysis liquid which depends on the presence of air bubbles in the dialysis liquid, and which is arranged downstream of a region to be monitored of the dialysis liquid circuit, in which during operation of the dialysis liquid circuit a negative pressure exists with respect to atmospheric pressure. The means furthermore comprise an evaluation unit which is connected with the gas sensor and which is configured such that the property measured by means of the gas sensor is evaluated with regard to the presence of air bubbles in the dialysis liquid.

The invention thus is based on the use of a gas sensor traversed by the dialysis liquid during operation of the dialysis liquid circuit, which is arranged downstream of the negative pressure region to be examined. The signal of the gas sensor is transferred to an evaluation unit which performs a signal evaluation. It is conceivable for instance that upon detection of leakages as a result of the sensor signal the evaluation unit emits an alarm signal or initiates certain operating modes of the dialysis liquid circuit. In accordance with the invention, this provides for a continuous detection of air bubbles in the dialysis liquid or a continuous monitoring of the dialysis liquid circuit for leakages, so that other than in the prior art errors are detected quickly and reliably.

In a further aspect of the invention it is provided that the gas sensor is arranged downstream of a dialyser located in the dialysis liquid circuit. Preferably, the gas sensor is disposed upstream of a pump which delivers the dialysis liquid and which effects the generation of negative pressure.

The gas sensor can for instance be a conductivity sensor. Such conductivity sensors have long since been used in dialysis liquid circuits, in order to determine the composition of the dialysis liquid. In accordance with the invention, these sensors known for a long time now can additionally be used to detect air bubbles in the dialysis liquid circuit as a gas sensor. In this way, an effective monitoring of the dialysis liquid circuit for leakages can be effected with a minimum of additional effort.

The conductivity of a liquid thus can be determined by means of a conductivity sensor, wherein for instance a flow measuring cell is used. In principle, the determination of the conductivity $\sigma$ of a homogeneous medium is effected by measuring the electrical resistance R between two contacts at a distance I, which are connected with each other by the conducting medium with a mean cross-sectional area A, according to the following relationship:

$$R = 1/\sigma \cdot l/A$$

and $$\sigma = 1/R \cdot l/A.$$

Since air is an insulator, the presence of air bubbles reduces the mean cross-sectional area A contributing to conduction in the measurement path, which results in that a greater electrical resistance R and hence a smaller conductivity $\sigma$ is detected.

In such conductivity sensor, the contact electrodes are disposed in a conduit portion such that they are in direct contact with the dialysis liquid. The conductivity advantageously is measured via the strength of an alternating current which flows through the dialysis liquid via the contact electrodes.

Apart from conductivity sensors, other sensors can also be used in accordance with the invention, which measure a property of the dialysis liquid which is changed by the presence of air bubbles. These include for instance optical sensors. The use of a capacitive sensor for detecting air bubbles is known from DE 196 51 355 A1.

It is conceivable that depending on geometry and measurement method the signal strength can be increased in the presence of air, as is the case for instance with absorption measurements in which the absorption is effected by water. It is likewise conceivable that the signal strength is reduced in the presence of air, as is the case for instance when light is scattered more in the presence of air bubbles or is deflected on its path to the detector. Since air bubbles generally are not homogeneously distributed in the air liquid, the occurrence of signal peaks is characteristic for the presence of air bubbles.

Of course, an averaged value, for instance a mean conductivity can also be used to infer the presence of air bubbles.

Correspondingly, it can be provided that the gas sensor is configured such that by means of the gas sensor individual air bubbles can be detected in the dialysis liquid. In this case it is required that the measurement can resolve shorter periods than the residence time of an air bubble in the volume of the gas sensor. Assuming that the air bubble moves with the same speed as the dialysis liquid, the time resolution of the gas sensor, i.e. the time resolution of the conductivity measuring cell, determines the reaction to the presence of air bubbles. If the sensor signal is sampled in intervals t shorter than the residence time T of an air bubble in the volume V of the sensor, the passage of an air bubble through the sensor cell causes a sharp drop in the signal measured. Thus:

$$T = V/Q, t < T,$$

wherein Q is the flow rate through the sensor cell. Typical values in a dialysis apparatus or dialysis liquid circuit, which do, however, not limit the invention, are V=2 ml, Q=500 ml/min, which results in a residence time T=0.2 s.

It is likewise conceivable that the gas sensor and/or the evaluation unit is configured such that a mean value of the at least one property of the dialysis liquid is detected and taken as a basis for the evaluation. If the sensor signal is averaged over a period t>T, short-term changes in the properties measured virtually can no longer be detected. Instead, a mean value of the property measured, for instance the conductivity, is available in the presence of air bubbles, which differs from the value that would be measured with the same liquid in the absence of air bubbles.

In a further aspect of the invention it is provided that the evaluation unit is configured such that it emits a signal and/or initiates a certain mode of operation of the dialysis liquid circuit or a dialysis apparatus which includes the dialysis circuit, when it is detected upon evaluation of the gas sensor signal representing the property measured that air bubbles exist in the dialysis liquid.

It is conceivable for instance that a pressure holding test of the dialysis liquid circuit is initiated. Thus, if due to the continuous measurement by the method of the invention air bubbles are detected in the dialysis liquid, the system can be stopped and a second measurement can be effected via the pressure holding test, e.g. for checking purposes, to avoid unnecessary warning messages, or to analyse the error. As a second measurement, in which a test volume specifically is exposed to certain pressure conditions and the course of pressure over time is detected, such pressure holding test can effectively be combined with the continuous monitoring, in order to ensure a both fast and reliable detection of leakages. For the pressure holding test, e.g. the liquid circuit can be stopped, the point to be examined can be sealed, and the course of pressure in time can be measured. If the negative pressure is reduced, this is an indication for the penetration of air into the dialysis liquid circuit and thus for a leakage. In this method known per se, pressure sensors and valves therefore are provided for sealing and limiting the region to be examined.

Furthermore, a warning possibly is issued to the user, when it is detected that air bubbles are present in the dialysis liquid.

In a further aspect of the invention, a bypass conduit is provided, which bypasses the region to be monitored, wherein at least one valve is provided, by means of which dialysis liquid can flow through the bypass conduit for performing a reference measurement when the valve is open. To be able to determine the property of the dialysis liquid in the absence of air bubbles, the same is guided around the region to be monitored by means of the bypass conduit and a property of the dialysis liquid is measured. On the basis of this reference value, a determination then can be performed as to whether air bubbles are present in the dialysis liquid after dialysis liquid has flown through the region to be monitored.

In a further aspect of the invention it is provided that upstream of the region to be monitored of the dialysis liquid circuit a further gas sensor is arranged for performing a reference measurement. Thus, a second gas sensor can be used before the region to be monitored, in order to measure the property, e.g. the conductivity of the dialysis liquid free from air bubbles. If upon flowing through the region to be monitored the property is changed as compared to the dialysis liquid free from air, this is an indication for an input of air, i.e. for a leakage. If there is a reduction e.g. of the conductivity with respect to said reference measurement, this allows to infer not only the presence of air, but also the amount of air entering.

In a further aspect of the invention it is provided that means for changing the pressure are arranged in the region to be monitored. A possible leakage can be detected by varying the negative pressure in the region to be monitored. Since in the case of a leak, the air penetration rate will increase with increasing pressure gradient, a decrease of the internal pressure will lead to an increased penetration of air. When the decrease of the internal pressure is caused by flow increase of a delivery pump located downstream of the negative pressure region, this can lead to the fact that the amount of inflowing air is increasing in absolute terms, but its amount relative to the total flow remains constant, so that there is no change in the property measured. Therefore, it is particularly advantageous when internal pressure and volume flow are uncoupled. For this purpose, it can be provided that upstream of the region to be monitored a pressure regulator is arranged, which is formed for instance by an adjustable valve or also by an adjustable pump.

In a further aspect of the invention it is provided that at least one pressure sensor for detecting the pressure existing in the dialysis liquid is arranged in the dialysis liquid circuit. In principle, different possibilities exist for the formation of air bubbles or gas bubbles inside the dialysis liquid. One possibility is the above-mentioned entry of air due to a leakage or another possibility is a post-degassing of the dialysis liquid. By means of a pressure sensor, preferably in the vicinity of the gas sensor, a distinction can be made between the two possibilities for the formation of gas bubbles. If the pressure lies above a negative pressure ($\geq 350$ mmHg) necessary for a massive post-degassing, the gas bubbles must have been formed by an external entry of air. In the case of a strong negative pressure, however, gas bubbles can have been formed by both possibilities (leakage, post-degassing).

Said post-degassing of the dialysis liquid chiefly occurs when degassing on the primary side was insufficient or a comparatively high $CO_2$ partial pressure exists in the dialysate due to a high bicarbonate content.

In contrast to an air detection alone by actuation of a secondary air separation, as it is known from the prior art, the detection in accordance with the present invention has the advantage that here air bubbles are detected immediately and one need not wait first for an accumulation in a secondary separator.

According to the previous solution, in which secondary air was separated downstream of the dialyser, no distinction is made between input of air and post-degassing. The previously known solution provides that for the case that a decrease of the liquid level in the air separation chamber is detected, the air is removed from the chamber by opening a valve or by a pump.

The present invention furthermore relates to a method for detecting air in a dialysis liquid flowing through a dialysis liquid circuit, in which downstream of a region to be monitored of the dialysis liquid circuit, in which during operation of the dialysis liquid circuit negative pressure exists with respect to atmospheric pressure, a property of the dialysis liquid flowing through a measurement region, i.e. a region for instance directly beside a gas sensor, is measured continuously, which depends on the presence of air bubbles in the dialysis liquid, wherein the property measured or a signal based thereon is evaluated with regard to the presence of air bubbles in the dialysis liquid. In particular, this advantageously is a method for monitoring the dialysis liquid circuit for leakages.

Preferably, the property measured is the conductivity of the dialysis liquid.

In a further aspect of the invention it is provided that individual signal peaks of the property, for instance individual signal peaks of the conductivity, are measured and that on this basis an evaluation is effected. Alternatively, it is also conceivable that a mean value of the property is formed and that on the basis of the mean value the evaluation is made.

As explained above, it can be provided that for the case that air bubbles in the dialysis liquid are determined, a signal is emitted and/or a certain mode of operation of the dialysis liquid circuit is initiated.

This can for instance be a pressure holding test of the dialysis liquid circuit. As described above, the same can be used as a second measurement for checking purposes. Other modes of operation, such as the interruption of the dialysis treatment and/or the output of a corresponding warning are conceivable.

As stated above, a reference measurement can be performed, by means of which the property in question, for instance the conductivity of the dialysis liquid free from air bubbles is determined.

The reference measurement can be performed in that dialysis liquid is guided around the region to be monitored in a bypass. It can also be performed in that the property of the dialysis liquid is measured upstream of the region to be monitored.

If no reference measurement is to be made or if no reference measurement is possible, air bubbles also can be inferred by varying the pressure in the region to be monitored, wherein it preferably is provided that the flow rate of the dialysis liquid is not varied.

The present invention furthermore relates to the use of a gas sensor in a dialysis liquid circuit, which is characterized in that the gas sensor serves to detect air bubbles in a dialysis liquid flowing through a dialysis liquid circuit and is configured such that it measures at least one property of the dialysis liquid, which depends on the presence of air bubbles in the dialysis liquid, wherein the gas sensor is arranged downstream of a region to be monitored of the dialysis liquid circuit, in which during operation of the dialysis liquid circuit a negative pressure exists with respect to atmospheric pressure, and is traversed continuously by the dialysis liquid. In particular, the gas sensor advantageously is used for monitoring the dialysis liquid circuit for leakages.

Preferred aspects of the use of a gas sensor in accordance with the invention are as described herein.

This invention finally relates to a dialysis apparatus with a dialysis liquid circuit as described herein.

The dialysis liquid, which is monitored for air bubbles in accordance with the invention, can be any liquid which in an operating phase of a dialysis apparatus flows through the dialysis liquid circuit, such as pure ultrafiltrate or also cleaning liquid. In these operating phases, too, the dialysis liquid circuit thus can also be monitored for leakages in accordance with the invention.

BRIEF DESCRIPTION OF THE DRAWINGS

Further details and advantages of the invention will be explained in detail with reference to an embodiment illustrated in the drawing, in which.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
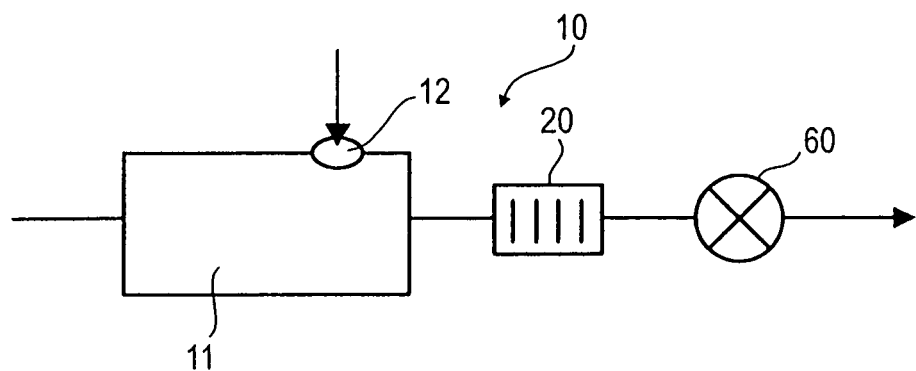
FIG. 1: shows a schematic representation of an arrangement for leak detection by conductivity measurement by means of signal peak detection.

FIG. 1 shows a schematic representation of the components of the dialysis liquid circuit in accordance with the invention, wherein the detection of leakages in the negative pressure region of the dialysis liquid circuit is effected by signal peak detection.

Reference numeral 10 designates the dialysis liquid circuit whose region 11 represents the region of the dialysis liquid circuit to be monitored for leakages. Downstream of the region 11 to be monitored the gas sensor 20 is disposed, which in the illustrated example is configured as a conductivity sensor. In particular, an often already existing conductivity sensor can be employed, which now is used additionally for detecting air bubbles in accordance with the invention.

Reference numeral 60 designates a pump arranged downstream of the region 11 to be monitored and downstream of the gas sensor 20. During operation of the pump, the region 11 to be monitored is located on the suction side of the pump, so that a negative pressure exists in the same.

Reference numeral 12 designates a leakage point of the region 11 to be monitored, through which air enters into the region 11 to be monitored, as is indicated by the arrow. This air forming air bubbles in the dialysis liquid flowing through the region 11 to be monitored now can be detected for instance by signal peak detection.

As explained above, the signal of the gas sensor 20 must be recorded with a sampling rate which is comparable with the residence time of an air bubble in the sensor 20. Air bubbles can be detected when they cause drops in conductivity which are greater than the noise of the conductivity measurement. The higher the conductivity of the liquid, the greater the effect of air bubbles which, as explained above, reduce the conductivity of the mixture of air and dialysis liquid. If the conductivity in the region 11 to be monitored is subject to fluctuations, e.g. due to fluctuations in the mixing system of the dialysis apparatus, air-induced signal peaks can be distinguished from conductivity fluctuations of the air-free liquid in that the latter take place at a distinctly slower rate. In general, a temperature compensation of the conductivity is not necessary, since the air-induced signal peaks are comparatively short and the temperature fluctuations influence the conductivity at a slower rate.

Figure 4:
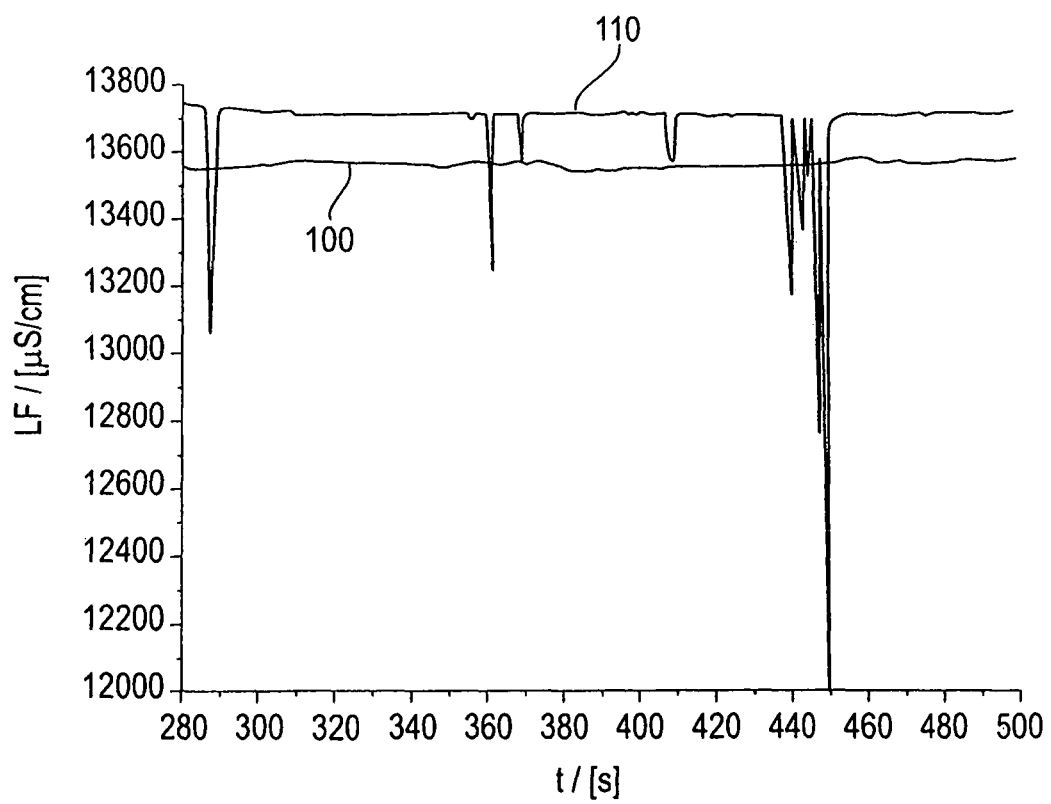
FIG. 4: shows the representation of the course of conductivity over time upstream and downstream of a dialyser.

In the arrangement shown in FIG. 1 it is possible to perform a signal peak detection, in which the conductivity is detected over time and in which signal peaks occur as a result of brief reductions in conductivity due to air bubbles. This is shown for instance in FIG. 4, in which signal peaks occurring at different times are illustrated. Line 100 extending approximately horizontally shows the conductivity upstream of the region to be monitored, for instance upstream of a dialyser, and line 110 including the signal peaks shows the conductivity downstream of the region to be monitored.

If a quantification of the input of air with the arrangement as shown in FIG. 1 is necessary, this requires a rough alignment of the conductivity cell, so that the number or amount of air bubbles can be inferred from the number or height of the signal peaks.

If a better signal-to-noise ratio should be achieved, the conductivity signal of the gas sensor can be averaged over an extended period. As a result of the longer averaging time it can happen that the air-induced conductivity signal peaks are no longer visible, but that only a reduction of the averaged conductivity value is present as compared to a dialysis liquid free from air bubbles. In this measurement method, a compensation of temperature influences is recommendable when measuring the respective property, i.e. for instance during the conductivity measurement, and also a good thermal insulation of the gas sensor with respect to environmental influences.

A detection of air bubbles is effected by alternate measurement of the conductivity in a condition in which definitely no air is present in the dialysis liquid, and in a condition in which the input of air in the system is possible.

Figure 2:
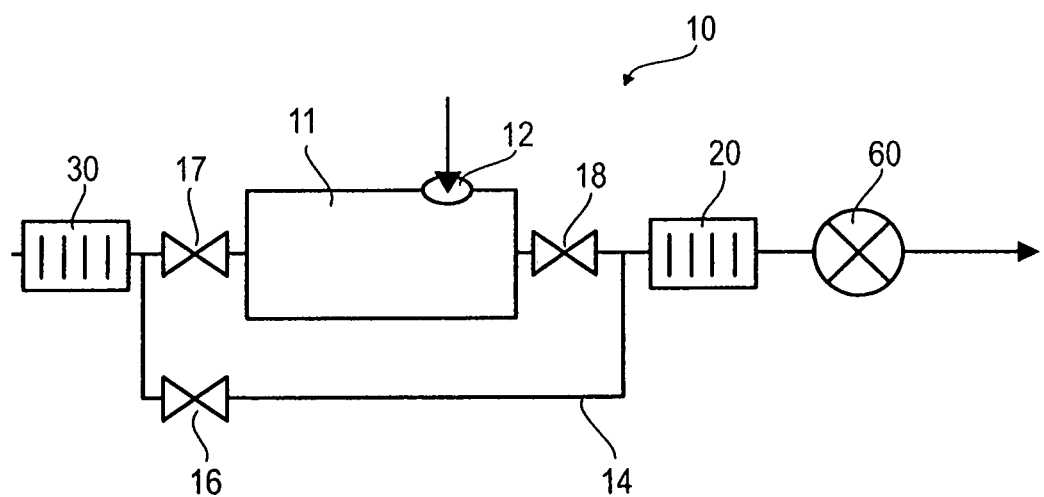
FIG. 2: shows a schematic representation of an arrangement for leak detection by determining the averaged conductivity by means of bypass conduit or second sensor.

FIG. 2 shows such an arrangement for leakage detection according to this principle, wherein identical or functionally equivalent components are designated with the same reference numerals as in FIG. 1.

First, the conductivity of the circulating dialysis liquid is determined in the absence of air bubbles, e.g. by measurement by means of the conductivity sensor 20 while bypassing the region 11 to be monitored by means of the bypass conduit 14. The same includes the valve 16, by means of which the bypass conduit 14 can be closed or opened. For the reference measurement, the valve 16 is opened and the valves 17, 18 disposed upstream and downstream of the region 11 to be monitored are closed. When the measured conductivity value of the dialysis liquid free from air bubbles is available, the valve 16 is closed and the region 11 to be monitored is traversed with open valves 17, 18. If the conductivity value measured by means of the sensor 20 then lies below that of the reference measurement, there is an input of air via the leakage point 12.

As an alternative, the reference measurement also can be effected continuously before the region 11 to be monitored with a second gas sensor 30, which in the embodiment shown here likewise is configured as a conductivity sensor. If upon traversing the region 11 to be monitored the conductivity at the gas sensor 20 is smaller than the conductivity of the liquid free from air bubbles, which is measured by means of the gas sensor 30, this is an indication for an input of air. From the reduction of conductivity with respect to the reference value, the amount of air entering via the leakage point 12 can be estimated.

Figure 3:
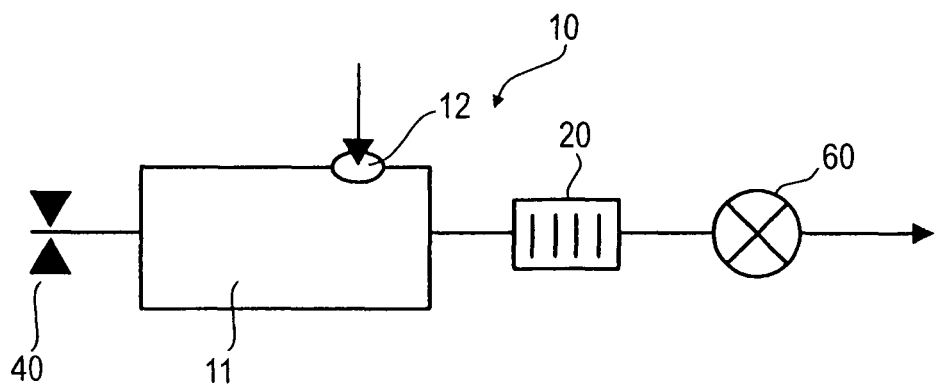
FIG. 3: shows a schematic representation of an arrangement for leak detection by determining the averaged conductivity by means of a change in pressure.

FIG. 3 shows an arrangement which can be used for instance when a reference measurement is not possible. In this case, a leakage can be detected by varying the negative pressure in the region 11 to be monitored. Identical or functionally equivalent parts of the arrangement are provided with the same reference numerals as in FIG. 1.

Reference numeral 40 designates a pressure regulator, by means of which the pressure conditions in the region to be monitored can be varied.

In the case of a leak 12 in the region 11 to be monitored, the penetration rate of the air increases with increasing pressure gradient between the surroundings and the region 11. The increase in the delivery rate of the pump 60 leads to an increased penetration of air by decrease of the internal pressure in the region 11.

Since the decrease of the internal pressure in the region 11 by flow increase of a delivery pump 60 located after the negative pressure region 11 can be proportional to the increase in the delivery rate, the amount of air flowing in through the leakage point 12 is absolutely greater in this case than with a smaller delivery rate of the pump 60, but the amount of inflowing air in relation to the total flow rate can remain constant, so that there is no change in conductivity in the final analysis. For this purpose, a pressure regulator 40 is provided upstream of the region 11, which can be configured in the form of an adjustable pump or an adjustable valve and by means of which uncoupling between internal pressure and volume flow is possible.

In the present invention, the dialysis liquid also can be pure ultrafiltrate, when e.g. in the arrangements shown in FIGS. 1 to 3 the supply line is closed. By means of the present invention a detection of air bubbles in the ultrafiltrate can of course also be effected for this case, in order to monitor the tightness of the corresponding liquid circuit.

The present invention advantageously can be used for monitoring the tightness of the parts of a dialysis liquid circuit, in which at least partly a negative pressure exists with respect to the surroundings. These regions of negative pressure can both be parts of the dialysis liquid circuit inside a dialysis apparatus and external dialysis liquid circuits with a dialyser. In this case especially leakages may occur during connection, which possibly cannot be detected before commencement of the treatment.

The term "dialysis liquid circuit" in accordance with the present invention should be interpreted broadly and can include both conduits for conducting dialysis liquid and components disposed in the conduits, such as the dialyser, pumps, etc. and also units connected therewith, such as controllers, said evaluation unit, etc.

The term "dialysis liquid" also should be interpreted broadly: It can be any liquid which flows through the dialysis liquid circuit in an operating phase of the dialyser, such as dialysate added, pure ultrafiltrate or also cleaning liquid which during cleaning flows through the dialysis liquid circuit. In accordance with the invention, the dialysis liquid circuit hence can be monitored for leakages in all operating phases.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A dialysis liquid circuit comprising:
   conduits for conducting a dialysis liquid, and elements for continuously detecting air in the dialysis liquid and leakage in the dialysis liquid circuit, the elements including
   at least one gas sensor traversed continuously by dialysis liquid, the at least one gas sensor being configured such that it measures at least one property of the dialysis liquid which depends on the presence of air bubbles in the dialysis liquid, and being arranged downstream of a region to be monitored of the dialysis liquid circuit in which during operation of the dialysis liquid circuit a negative pressure exists with respect to atmospheric pressure, and
   an evaluation unit which is connected with the gas sensor and is configured such that the property measured via the gas sensor is evaluated with regard to the presence of air bubbles in the dialysis liquid and based thereon, with regard to the presence of leakage in the dialysis liquid circuit.

2. The dialysis liquid circuit according to claim 1, further comprising a dialyser arranged in the dialysis liquid circuit, and wherein the gas sensor is arranged downstream of the dialyser.

3. The dialysis liquid circuit according to claim 1, wherein the gas sensor is a conductivity sensor.

4. The dialysis liquid circuit according to claim 1, wherein the gas sensor is configured such that via the gas sensor individual signal peaks of the property of the dialysis liquid can be detected.

5. The dialysis liquid circuit according to claim 1, wherein at least one of the gas sensor and the evaluation unit is configured such that a mean value of the at least one property of the dialysis liquid is determined and taken as a basis for evaluation.

6. The dialysis liquid circuit according to claim 1, wherein the evaluation unit is configured to at least one of emit a signal and initiate a particular mode of operation of the dialysis liquid circuit when it is detected during the evaluation that air bubbles are present in the dialysis liquid.

7. The dialysis liquid circuit according to claim 6, wherein the particular mode of operation is a pressure holding test of the dialysis liquid circuit or of the region to be monitored.

8. The dialysis liquid circuit according to claim 1, further comprising
   a bypass conduit, which bypasses the region to be monitored, and
   at least one shut-off valve, in whose open condition the dialysis liquid can flow through the bypass conduit for performing a reference measurement.

9. The dialysis liquid circuit according to claim 1, further comprising, arranged upstream of the region to be monitored of the dialysis liquid circuit, another gas sensor for performing a reference measurement.

10. The dialysis liquid circuit according to claim 1, further comprising an element for varying the pressure in the region to be monitored.

11. The dialysis liquid circuit according to claim 10, wherein the element for varying the pressure includes a pressure regulator arranged upstream of the region to be monitored and a pump arranged downstream of the region to be monitored.

12. The dialysis liquid circuit according to claim 11, wherein the pressure regulator is configured as an adjustable valve or an adjustable pump.

13. The dialysis liquid circuit according to claim 1, wherein in the dialysis liquid circuit at least one pressure sensor is arranged for detecting the pressure existing in the dialysis liquid.

14. A dialysis apparatus with at least one dialysis liquid circuit according to claim 1.

* * * * *